US012040500B2

(12) United States Patent
Specht

(10) Patent No.: US 12,040,500 B2
(45) Date of Patent: Jul. 16, 2024

(54) SENSOR ASSEMBLY COMPRISING CONFORMABLE BATTERY PACK

(71) Applicant: DURACELL U.S. OPERATIONS, INC., Wilmington, DE (US)

(72) Inventor: Steven J. Specht, Brookfield, CT (US)

(73) Assignee: DURACELL U.S. OPERATIONS, INC., Wilmington, DE (US)

( * ) Notice: Subject to any disclaimer, the term of this patent is extended or adjusted under 35 U.S.C. 154(b) by 93 days.

(21) Appl. No.: 17/451,141

(22) Filed: Oct. 15, 2021

(65) Prior Publication Data

US 2022/0123408 A1 Apr. 21, 2022

Related U.S. Application Data

(60) Provisional application No. 63/093,781, filed on Oct. 19, 2020.

(51) Int. Cl.
*H01M 50/216* (2021.01)
*H01M 10/42* (2006.01)
*H01M 50/136* (2021.01)
*H01M 50/238* (2021.01)
*H01M 50/502* (2021.01)

(52) U.S. Cl.
CPC ....... *H01M 50/216* (2021.01); *H01M 10/425* (2013.01); *H01M 50/136* (2021.01); *H01M 50/238* (2021.01); *H01M 50/502* (2021.01); *H01M 2220/30* (2013.01)

(58) Field of Classification Search
CPC ............ H01M 50/216; H01M 50/502; H01M 50/136; H01M 50/238; H01M 10/425; H01M 2220/30
See application file for complete search history.

(56) References Cited

U.S. PATENT DOCUMENTS

| | | | |
|---|---|---|---|
| 3,735,766 A * | 5/1973 | Bowers | A61N 1/37512 607/36 |
| 5,531,601 A | 7/1996 | Amoroso | |
| 9,343,716 B2 | 5/2016 | Rothkopf et al. | |
| 11,728,491 B2 | 8/2023 | Furutani et al. | |
| 2011/0160641 A1* | 6/2011 | Ueda | H01M 50/51 604/20 |
| 2015/0373831 A1 | 12/2015 | Rogers et al. | |
| 2016/0204390 A1 | 7/2016 | Choi et al. | |
| 2019/0388667 A1 | 12/2019 | Xu | |

FOREIGN PATENT DOCUMENTS

| | | |
|---|---|---|
| EP | 2306549 A1 | 4/2011 |
| KR | 100875109 B1 | 12/2008 |
| WO | WO-2006/105050 A2 | 10/2006 |

OTHER PUBLICATIONS

International Application No. PCT/US2021/055129, International Search Report and Written Opinion, mailed Jan. 28, 2022.

(Continued)

*Primary Examiner* — Jane J Rhee

(57) ABSTRACT

A battery pack assembly includes an array of individual electrochemical cells electrically connected to one another. The array of individual electrochemical cells is embedded and encapsulated by a matrix of conformable material and the matrix of conformable material provides a protective outer shell. A sensor is electrically connected to the array.

15 Claims, 7 Drawing Sheets

(56) References Cited

OTHER PUBLICATIONS

Schiller et al., Development of a stretchable battery pack for wearable applications, Master Thesis to obtain the academic degree of Diplom-Ingenieur in the Master's Program, Master Thesis, Johannes Kepler University Linz (Nov. 2019).

Atieh, Design, modeling, fabrication and testing of a pieroresistive-based tactile sensor for minimally invasive surgery applications, A thesis in the Department of Mechanical and Industrial Engineering, Concordia University, downloaded from the Internet at: <https://citeseerx.ist.psu.edu/viewdoc/download?doi=10.1.1.633.1168&rep=rep1&type=pdf> (2012).

Prochowicz et al., Correlation of recombination and open circuit voltage in planar heterojunction perovskite solar cells, J. Mater. Chem. C, 7:1273-9 (2019).

Smooth-On SDS and technical bulletings (TB/TDS). Smooth-On (n.d.). downloaded from the Internet at: <https://www.smooth-on.com/documents/> (2024).

U.S. Appl. No. 17/451,147, Nonfinal Office Action, Jan. 18, 2024.

* cited by examiner

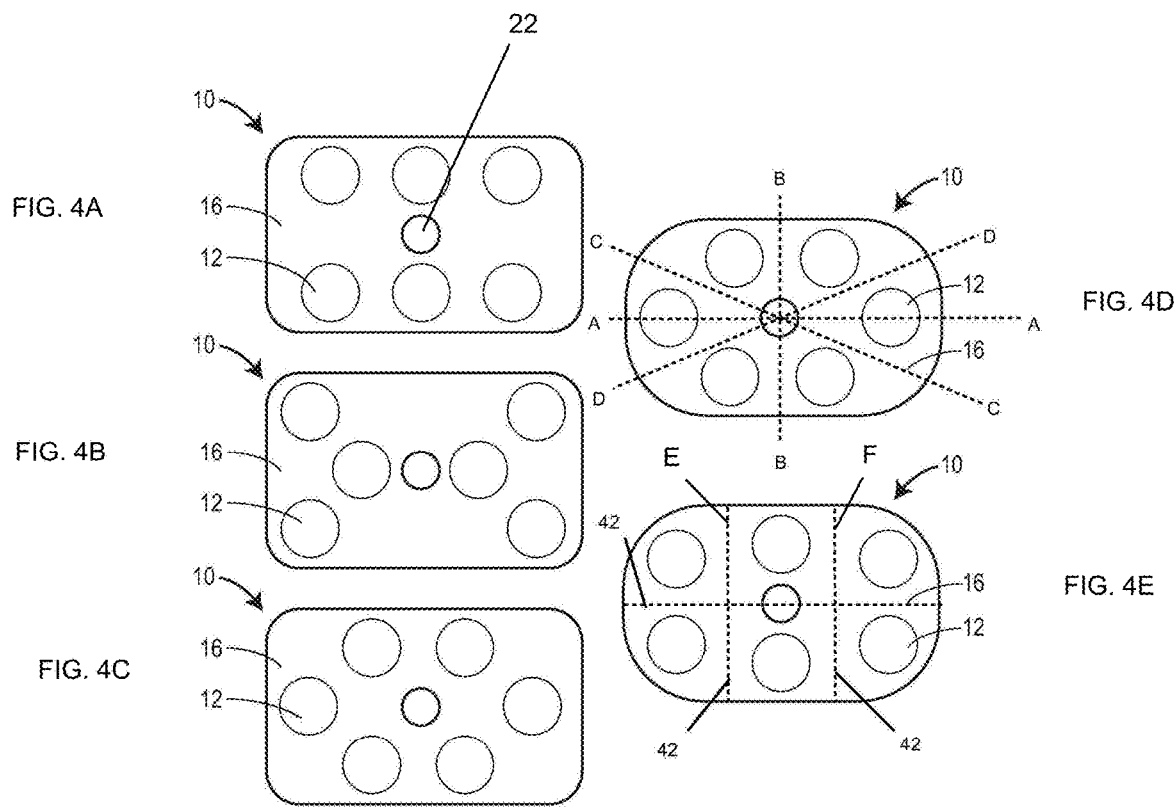
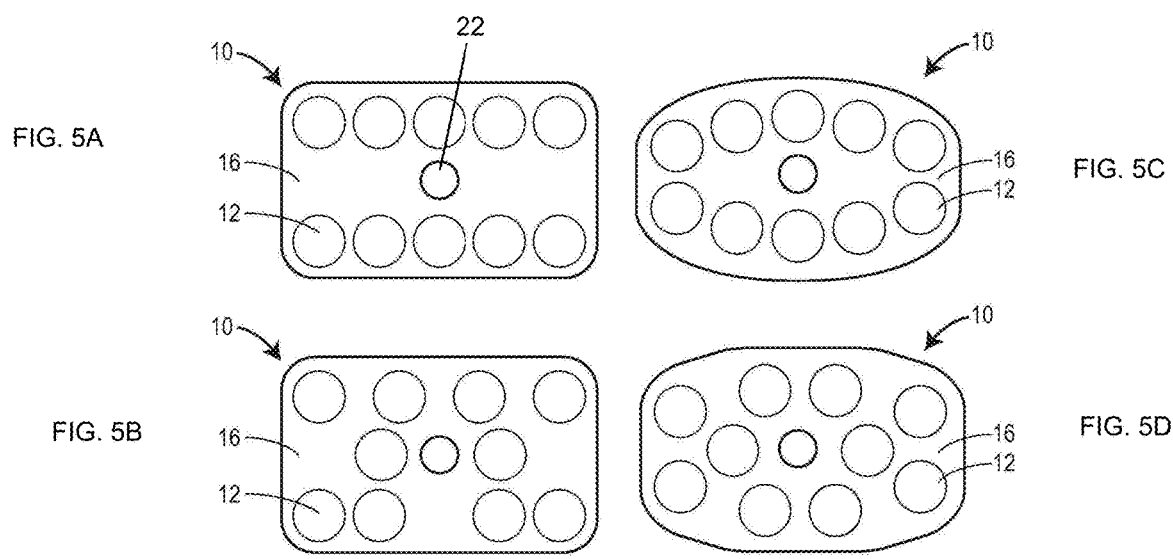

SENSOR ASSEMBLY COMPRISING CONFORMABLE BATTERY PACK

FIELD OF THE DISCLOSURE

The disclosure relates to portable or wearable battery packs and more specifically to conformable battery pack assemblies comprising a sensor.

BACKGROUND

Portable consumer electronic devices have certain power requirements. Generally, small, wearable consumer electronic devices receive power from a single battery (contained within the device itself), or from a portable battery pack that may include one or more battery cells. These portable battery packs are usually contained within a hard plastic outer shell that may be attached to a user by a strap, or carried by a user in a pocket or other carrying location. These hard battery packs are uncomfortable when secured to the body with a strap or carried in a pocket. Additionally, such battery packs create bulges in clothing when worn under the clothing, which may be undesirable aesthetically, as well as being uncomfortable. Moreover, current battery packs require an inconvenient connection cord to supply power to the device.

Battery assemblies containing a plurality of cells with top and bottom laminate layers coupled to the cells with an adhesive that allows flexibility and the possible removal of one or more cells to better fit in devices are described in U.S. Pat. No. 9,343,716. These battery assemblies are arranged such that top and bottom laminate layers are connected to the cells and each other by adhesives.

SUMMARY OF THE DISCLOSURE

According to some embodiments, a battery pack assembly includes an array of individual electrochemical cells electrically connected to one another. The array of individual electrochemical cells is embedded in and encapsulated by a matrix of conformable material and the matrix of conformable material provides a flexible outer shell. An electronic component is electrically connected to the array. The foregoing embodiment of a battery pack assembly may further include any one or more of the following optional features, structures, and/or forms.

In some optional forms, the electrical component is a sensor, such as a physiological sensor.

In other optional forms, the electronic component comprises a one of heart rate sensor, a temperature sensor, or an EKG sensor.

In other optional forms, the battery pack assembly further comprises a drug delivery system that is activated by a signal from the electronic component.

In other optional forms, a direct and continuous interconnection is formed between the array of electrochemical cells battery pack assembly and the electronic component.

In other optional forms, the flexible outer shell comprises an outer shell material including a failure stretch ratio of 1.1 to 1.8, an ultimate tensile strength between 1.0 MPa and 50 MPa, and/or a Young's modulus of between 0.5 kPa and 140 kPa.

In other optional forms, the flexible outer shell material comprises an elastomer.

In other optional forms, the outer shell material is laminated around the individual electrochemical cells.

In other optional forms, an adhesive is disposed on one side or both sides of the flexible outer shell.

In other optional forms, the conformable material is molded around the electrochemical cells.

In other optional forms, the flexible outer shell material has a hardness as defined by ASTM D2240-15 of between HOOO-S 10 and 90A, preferably between HOO-5 and 30A, and more preferably between OO-10 and OO-50.

In other optional forms, the outer shell material has an elongation break between 10% and 1,000%.

In other optional forms, the electronic component comprises one or more of a processor, a microprocessor, a signal processor, an integrated circuit, a display, a capacitor, a resistor, a transistor, a medical application device such as a glucose delivery device or an automatic defibrillator, a global positioning system (GPS) receiver, a sensor (such as a biometric sensor, a temperature sensor, an accelerometer, a moisture sensor), or an antenna.

In other optional forms, the electronic component is operably connected to a face of one electrochemical cell in the array of individual electrochemical cells.

In other optional forms, the electronic component is positioned within the flexible outer shell.

In other optional forms, the electronic component is surrounded and encapsulated by the flexible outer shell.

BRIEF DESCRIPTION OF THE DRAWINGS

While the specification concludes with claims particularly pointing out and distinctly claiming the subject matter, which is regarded as forming the present invention, the invention will be better understood from the following description taken in conjunction with the accompanying drawings.

FIGS. 4A-4E are top views of various additional embodiments of a battery pack assembly having a plurality of electrochemical cells with a first size.

FIGS. 5A-5D are top views of various additional embodiments of a battery pack assembly having a plurality of electrochemical cells with a second size.

DETAILED DESCRIPTION

Figure 1:
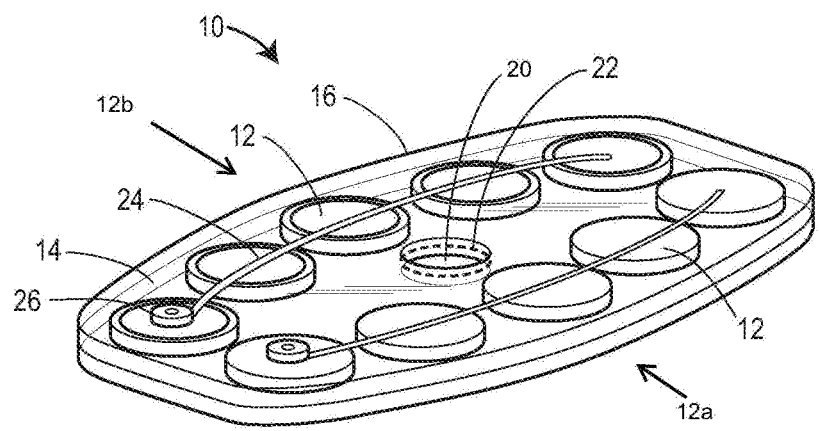
FIG. 1 is a top perspective view of a battery pack assembly constructed in accordance with the disclosure.

Electrochemical cells, or batteries, may be primary or secondary. Primary batteries are meant to be discharged, e.g., to exhaustion, only once and then discarded. Primary batteries (or disposable batteries) are described, for example, in David Linden, *Handbook of Batteries* (4$^{th}$ ed. 2011). Secondary batteries (or rechargeable batteries) are intended to be recharged and used over and over again. Secondary batteries may be discharged and recharged many times, e.g., more than fifty times, a hundred times, or more. Secondary batteries are described, for example, in David Linden, *Handbook of Batteries* (4$^{th}$ ed. 2011). Accordingly, batteries may include various electrochemical couples and electrolyte combinations. The description and examples provided herein apply to both primary and secondary batteries of aqueous, nonaqueous, ionic liquid, and solid state systems. Primary and secondary batteries of the aforementioned systems may be used in the battery pack assemblies according to the disclosure.

As used herein, the term "embedded in and encapsulated by" refers to an individual item such as a battery cell is completely embedded within a matrix of material so that substantially no gap or space exists between the embedded item and the matrix of material (e.g., the matrix of material contains less than 5% by volume of entrapped air/gas). In other words, the matrix of material is in contact with the embedded object at substantially all locations on the exterior of the embedded object. Examples of processes that produce items that are embedded in and encapsulated by a matrix of material include, for example, overmolding, dipping, spraying, casting, and vapor deposition.

As used herein, the term "surrounded and encapsulated" refers to an item, such as a battery cell, is completely surrounded by a matrix of material, but there may be a small gap or space between the item and the surrounding matrix of material. Examples of processes that produce surrounded and encapsulated items include, for example, lamination, vacuum forming, compression molding, powder coating, and bonding by enclosing the cells within an assembly of at least two pre-formed substrates and bonding at the seams with heat sealing or an adhesive.

The term "bending axis," "bending axes," "axis of bending," or "axes of bending" as used herein refers to one or more substantially straight lines that extend through a flexible outer shell of a battery pack without contacting any battery cells in the flexible outer shell. The bending axis or bending axes allow deformation or bending of the flexible outer shell along the substantially straight lines to readily form non-planar shapes, and thereby significantly enhances a user's comfort when a battery pack is applied to the user's skin. The bending axis or bending axes also allow deformation or bending of the flexible outer shell to conform with non-planar objects. A substantially straight line is a line that diverges by 20 degrees or less from straight, preferably 15 degrees or less, from an idealized line formed by drawing a straight line between the two end points of the bending axis at the perimeter edge of the flexible outer shell, wherein the divergence is measured by establishing an angled cone, beginning at one of the end points and extending 20 degrees (or 15 degrees) on either side of the idealized line such that the bending axis falls within this cone along its entire length. Material in the flexible outer shell advantageously is adapted to deform along the substantially straight line in response to bending forces that are applied to the flexible outer shell. The bending axis may extend along a length, width, and/or thickness dimension of the flexible outer shell. In some cases, an axis of symmetry may also be a bending axis if the axis of symmetry does not intersect or overlap with a battery cell disposed in the flexible outer shell.

As used herein, the term "electronic component" refers to any device powered by electricity. Examples of electronic components include processors, microprocessors, signal processors, integrated circuits, displays, capacitors, resistors, transistors, medical application devices (such as a glucose delivery device or an automatic defibrillator), global positioning system (GPS) receivers, sensors (such as biometric sensors, temperature sensors, accelerometers, moisture sensors), antennas, and combinations of the foregoing.

Many wearable electronic devices require a self-contained portable power supply. Typically, power is provided by an electrochemical battery cell or a portable battery pack assembly. However, existing electrochemical battery cells and battery pack assemblies are not sufficiently flexible and stretchable to be comfortable when attached to human skin and thus frequently result in an uncomfortable feel for the user.

Known battery assemblies that contain a plurality of cells with top and bottom laminate layers coupled to the cells with an adhesive generally lack flexibility, stretchability, and conformability.

The battery pack assemblies described herein provide a wide range of power characteristics while being flexible and conformable to advantageously enhance user comfort. The battery pack assemblies described herein also include a protective flexible outer shell having a skin-like feel, further advantageously enhancing user comfort and thereby extending the length of time the battery pack assemblies may be comfortably tolerated when worn. Furthermore, the described battery pack assemblies may be incorporated into articles of clothing, such as wrist bands, belts, suspenders, headbands, arm bands, socks, vests or other smart clothing in general to provide additional energy storage for rechargeable devices, health and fitness equipment, other sensors, audio equipment, and mobile phone power. Because the described battery pack assemblies may completely enclose the individual electrochemical cells within a matrix of waterproof conformable material, smart clothing incorporating the disclosed battery pack assemblies may advantageously be laundered safely, without having to remove the electrochemical cells.

Although the disclosed battery pack assemblies may comprise any type of electrochemical cell, in some examples, relatively low-cost coin or button electrochemical cells of any chemistry (including for example, Li-Primary, Zn—Ag$_2$O, Zn—MnO$_2$, and the like) may be advantageously employed. In other embodiments, the electrochemical cells may comprise cylindrical, prismatic, or pouch cells. In yet other embodiments, the electrochemical cells may comprise other shapes, such as rectangular or square shapes.

Figure 2:
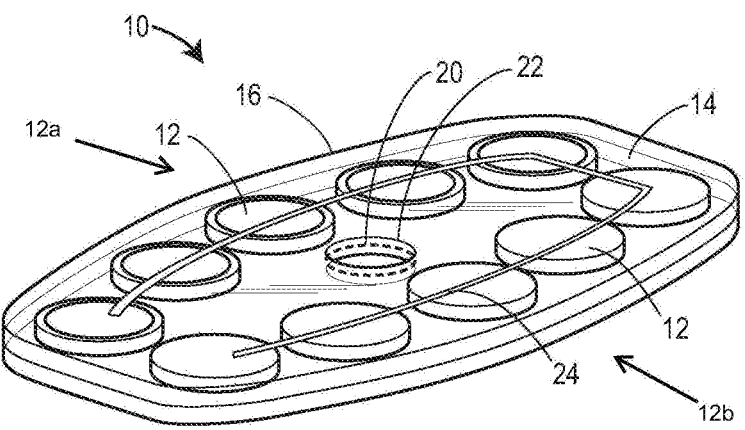
FIG. 2 is a bottom perspective view of the battery pack assembly of FIG. 1.
Figure 3:
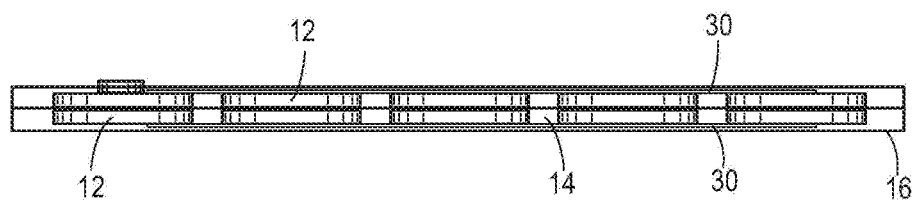
FIG. 3 is a side view of the battery pack assembly of FIG. 1.

Turning now to FIGS. 1-3, one example of a battery pack assembly 10 according to the disclosure comprises an array of individual electrochemical cells 12 that are electrically connected to one another. The array of individual electrochemical cells 12 is embedded in and encapsulated by a matrix of conformable material 14 that forms a protective and flexible outer shell 16 to thereby protect the cells from the ambient atmosphere as well as provide a conformable material that enhances user experience and comfort when the battery pack assembly is being worn. In the illustrated embodiment, an electronic component 20, such as an electronic component 20, is located in an opening 22 formed in the conformable material 14 such that the sensor may be in direct contact with the user's skin. In other embodiments, the electronic component 20 may be located in a separate compartment and embedded and encapsulated in the conformable material 14. Regardless, the electronic component 20 is also electrically connected to one or more of the electrochemical cells 12 to receive power. The electronic component 20 may comprise one or more of a processor, a microprocessor, a signal processor, an integrated circuit, a display, a capacitor, a resistor, a transistor, a sensor, a medical application device such as a glucose delivery device or an automatic defibrillator, a global positioning system (GPS) receiver, a sensor (such as a biometric sensor, a temperature sensor, an accelerometer, a moisture sensor), an induction coil, or an antenna. Furthermore, an antenna in some embodiments may be arranged such that it can also function as an induction coil that converts a time varying magnetic field or electrical field into a direct current for battery charging. In some embodiments, the electronic component 20 may be a sensor in direct contact with the user's skin. In other embodiments, the electronic component 20 may be located in a separate compartment and embedded and encapsulated in the conformable material 14. Regardless, the electronic component 20 is also electrically connected to one or more of the electrochemical cells 12 to receive power. The electronic component 20 is an optional component. The conformable battery pack assembly 10 may be used to power other devices that are not sensors in other embodiments.

In some embodiments, the electronic component may be connected to a face of a cell 12, or may be located within the matrix of conformable material 14 (e.g., embedded and encapsulated, or surrounded and encapsulated, by the matrix of conformable material) between cells 12 or between one cell 12 and an outer surface of the matrix of conformable material 14. The electronic component and the array of individual electrochemical cells 12 may be embedded in and encapsulated by the matrix of conformable material 12, for example by molding or covering with a film, to form an entire electronics/battery assembly. In yet other embodiments, stretchable (elastomeric) circuits with conductors and components may also be embedded in and encapsulated by the matrix of conformable material 14. Such embodiments produce a single integrated flexible/elastic unit comprising both electronic components and a power supply (the electrochemical cells 12), all of which are protected by the matrix of conformable material 14.

In some embodiments, the electrochemical cells 12 are connected in series and parallel to one another by flexible conductors 24 that electrically connect the respective electrochemical cells 12. While the illustrated embodiment includes two flexible conductors 24 on the top (FIG. 1), one connecting negative terminals of a first group 12b of the electrochemical cells 12 and the other connecting positive terminals of a second group 12a of electrochemical cells and one flexible conductor 24 on the bottom (FIG. 2), connecting the negative terminals of the second group 12a of the electrochemical cells 12 to the positive terminals of the first group 12b of electrochemical cells 12, such that the two groups 12a and 12b of electrochemical cells are arranged in series, while the individual electrochemical cells 12 in each group 12a, 12b are connected in parallel, the flexible conductors are for illustration purposes only. Thus, the electrochemical cells 12 may be electrically connected by the flexible conductors 24 in series, in parallel, or in series and in parallel as is known in the art, depending on power, capacity, and/or Voltage requirements. Optionally, one or more external terminals 26 may be used to connect the electrochemical cells 12 to a device needing power. The electronic component 20 may be electrically connected to the array of electrochemical cells 12 by the flexible conductor 24 internally (such that the sensor is disposed at least partially within the conformable material) or the electronic component 20 may alternatively be connected to the array of chemical cells 12 by the flexible conductor 24 externally at one or more of the external terminals 26.

The electronic component 20 may be virtually any type of sensor. In some embodiments, the electronic component 20 may be a physiological sensor that measures a physiological characteristic or condition. Representative example sensors include, but are not limited to, heart rate sensors, EKG sensors, nerve impulse sensors, glucose sensors, galvanic skin response sensors, hydration sensors, sweat sensors, and body temperature sensors, although virtually any type of sensor could be used. The battery pack assemblies 10 may also further comprise structure or a medical device capable of providing treatment for a sensed condition, such as a drug delivery system that is activated by a signal from the electronic component 20 (for example, an injection of insulin in response to glucose monitoring), electrical therapy for an abnormal heart rate (such as defibrillation), wound sterilization, and healing (e.g., bone growth stimulation), as further described with reference to FIG. 12.

In other embodiments, the electronic component 20 may be a location sensor or a biometric sensor. Representative sensors include, but are not limited to, a GPS sensor, an accelerometer, a gyroscope, a pedometer, etc. In representative examples, these types of sensors may be used in battery pack assemblies that are combined with sportswear to monitor sports performance. In other embodiments, the battery pack assembly with a location sensor, an accelerometer, and/or a moisture sensor may be affixed to a non-planar surface of a package for shipment tracking.

The flexible outer shell 16 comprises an outer shell material having a skin-like feel for enhancing and facilitating user comfort. The outer shell material comprises a material having one or more of the following characteristics: a failure stretch ratio of 1.1 to 1.8, preferably between 1.2 and 1.7, and more preferably between 1.3 and 1.6; an ultimate tensile strength between 1 and 50 MPa, preferably between 15 and 40 MPa, more preferably between 20 and 40 MPa, and more preferably between 25 and 35 MPa; or a Young's modulus of between 5 kPa and 140 MPa, preferably between 20 MPa and 100 MPa, and more preferably between 30 MPa and 80 MPa.

In some embodiments, the outer shell material comprises a hardness value as defined by ASTM Standard D2240-15 between HOOO-S 10 and 90A, preferably between HOO-5 and 30A, and more preferably between HOOO-10 and HOO-50. In other embodiments, the hardness may be greater than HOOO-S 10, or less than 90A, preferably between HOOO-S 10 and 90A.

In some embodiments, the outer shell material comprises an elongation break between 350% and 1,000%, preferably an elongation break between 500% and 900%, more preferably between 600% and 900%, and more preferably approximately 900%. In other embodiments, the elongation break may be greater than 350%, or less than 1,000%, preferably between 100% and 1500%.

In some embodiments, the outer shell material comprises a 100% modulus (i.e., tensile stress at 100% elongation) of less than 86 psi, preferably a 100% modulus between 8 psi and 86 psi, and more preferably about 10 psi.

In some embodiments, the outer shell material comprises a tensile strength of less than 50 MPa, or a tensile strength of greater than 15 MPa, preferably a tensile strength of between 15 and 40 MPa, and more preferably about 25 MPa.

In some embodiments, the outer shell material comprises an elastomer. Elastomers in the form of liquid precursors may be used to embed and encapsulate the individual electrochemical cells 12, for example by pouring the liquid elastomer into a mold that contains the electrochemical cells 12 connected together by the flexible conductors 24, and then by curing the elastomer (for example by drying or heating or letting a two-part liquid elastomer cure over time and/or temperature or by exposure to UV light or radiation). The liquid elastomer may alternatively be applied by dipping or spraying the electrochemical cells 12 and then initiating the curing process. In some embodiments, silicone rubbers suitable for casting, similar to those used for skin effects and movie effects may be particularly advantageous. Suitable silicone rubbers suitable for casting include, but are not limited to BODY DOUBLE™ Silk (Bentley Advanced Materials), BODY DOUBLE™ Standard Set (Bentley Advanced Materials), PlatSil® Gels (Polytek Development Corp.), ECO FLEX™ Series Silicone Rubbers (Smooth On, Inc.), Smooth-On Dragon Skin™ (Smooth-On, Inc.), or ELASTOSIL® RTV-2 (Wacker). Other materials including other silicones, or other materials, having the characteristics described herein may also be used. In other embodiments, hot melt glues or low pressure molding materials, such as Henkel Technomelt® AS 8998 polyolefin hot melt adhesive having an elongation break of 733% and a hardness of Shore 10A, may be used to embed and encapsulate the array of electrochemical cells.

Encapsulation can also be achieved by covering the electrochemical cells 12 with thin sheets of elastomeric substrates that are held together with adhesives. In some embodiments, the borders of the substrates and/or the areas around the edges of the batteries may be heat sealed to secure the electrochemical cells 12 in place. For example, the electrochemical cells 12 may be placed on a sheet of thin elastomer coated with an adhesive and then wired together with the flexible conductors 24. Another layer of adhesive coated elastomer film may then be pressed on top of the electrochemical cells 12, thereby providing a matrix of conformable material fully surrounding and encapsulating the electrochemical cells 12. The flexible conductors 24 may exit the encapsulation along the bond line between the two adjacent adhesive layers or at another desired location. In some embodiments, tapes such as 3M Schotchwrap® tape 50 with an elongation break of 200% or 3M Industrial Protective film 7070UV with an elongation break of 635%, may be used to surround and encapsulate the array of electrochemical cells.

Figure 10:
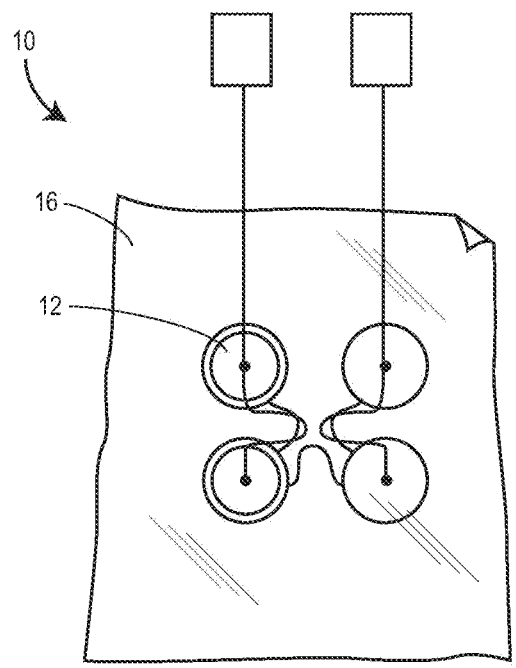
FIG. 10 is a top view of an alternate battery pack assembly having a laminated flexible outer shell.
Figure 11:
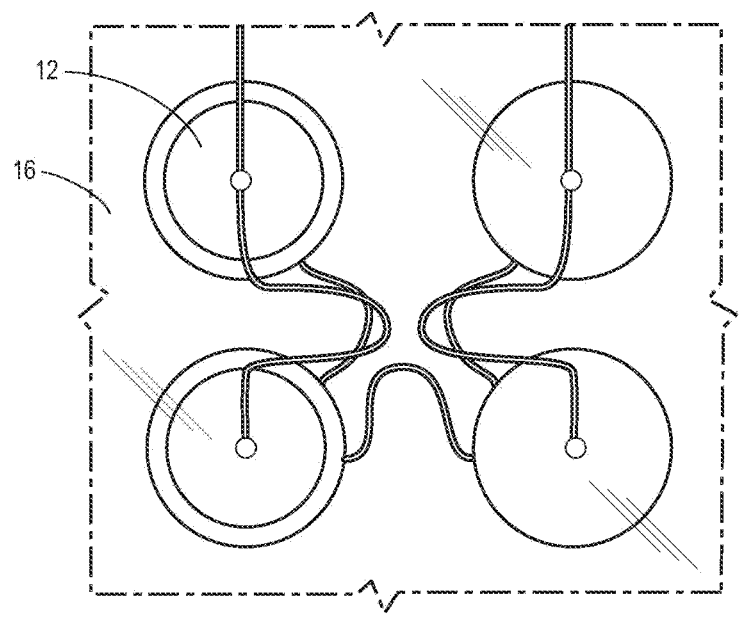
FIG. 11 is a close-up view of the electrochemical cells of the battery pack assembly of FIG. 10.

In some embodiments, the flexible outer shell material is laminated around the individual electrochemical cells 12 so that the individual electrochemical cells 12 are surrounded and encapsulated by the outer shell material, as illustrated in FIGS. 10 and 11. In other embodiments, the outer shell material is molded around the individual electrochemical cells so that the individual electrochemical cells 12 are embedded and encapsulated by the outer shell material, as illustrated in FIGS. 1-3.

In some embodiments, the outer shell material comprises an adhesive 30 (FIG. 3) on one or both sides.

Turning now to FIGS. 4A-4E, the disclosed battery pack assemblies 10 may have virtually endless outer shapes and electrochemical cell 12 array configurations. For example, for an electrochemical cell 12 having a first size or diameter, the outer shell material 16 may have a generally rectangular shape, or a more oblong/oval or circular shape (although other shapes are possible). The individual electrochemical cells 12 may be arranged to have a symmetrical (as illustrated) or non-symmetrical layout. The flexible outer shell material 16 may include the opening 22 for the electronic component 20. The electrochemical cells 12 may be arranged such that the array has one or more axes of symmetry. Preferably the array has at least three or more axes of symmetry. For example, the array may have, as illustrated in FIG. 4D, a first axis of symmetry A, a second axis of symmetry B, a third axis of symmetry C, and a fourth axis of symmetry D. In some examples, an axis of symmetry may form an axis of bending if the axis of symmetry does not touch an electrochemical cell, such as axes of symmetry B, C, and D in FIG. 4D. The axes of symmetry may be all non-parallel with one another. In other embodiments, two or more axes of symmetry may be parallel, but separated from one another, such as axes of symmetry E and F in FIG. 4E. In other embodiments more or less than four axes of symmetry may be formed.

The individual cells may be spaced from one another between 5% and 100%, preferably between 10% and 100%, and more preferably between 15% and 100% of an average cell diameter. In other embodiments, where the individual cells are rectangular or square in shape, the individual cells may be spaced from one another between 5% and 100%, preferably between 10% and 100%, of the largest linear dimension of the individual cells. Spacing in these ranges enhances bendability and conformability of the battery pack.

Additionally, the flexible outer shell may have a thickness to length ratio of between 1:2 and 1:30, preferably between 1:5 and 1:20, and more preferably between 1:10 and 1:15.

As illustrated in FIGS. 5A-5D, the disclosed battery pack assemblies 10 may have different electrochemical cell 12 array configurations when electrochemical cells 12 having a second size or diameter (in this case relatively smaller than the electrochemical cells 12 illustrated in FIGS. 4A-4E) are used. While the flexible outer shell material 16 shapes may be virtually endless, as in the embodiments of FIGS. 4A-4E, when smaller electrochemical cells 12 are used, more individual electrochemical cells 12 may be disposed in a given volume of outer shell material 16 because the individual electrochemical cells 12 may be more tightly packed together. In other embodiments, the battery pack assembly may include a mix of different sized and/or shaped electrochemical battery cells. Similar to the embodiments of FIGS. 4A-4E, the embodiments of FIGS. 5A-5D may also include the openings 22 for sensors 20.

Generally, more axes of bending, which may or may not correlate with axes of symmetry, accommodate more skin bending modes and thus advantageously a more comfortable fit for a user. Circular, hexagonal, or octagonal (more generally polygonal) packed arrays may be preferred, such as the arrays illustrated in FIGS. 4C-4E. Slits, cuts or perforations in the outer shell material 16 may produce greater flexibility or elasticity for the battery pack assembly 10. The slits, cuts, or perforations 42, illustrated for example in FIG. 4E, may be made between adjacent cells, for example, the slits may preferably be equidistant from, disposed between, or arranged along the axes of bending to provide enhanced conformability, or at other locations that reduce the stress in the encapsulation material and lower the forces required for bending or stretching the battery pack assembly 10.

Figure 6:
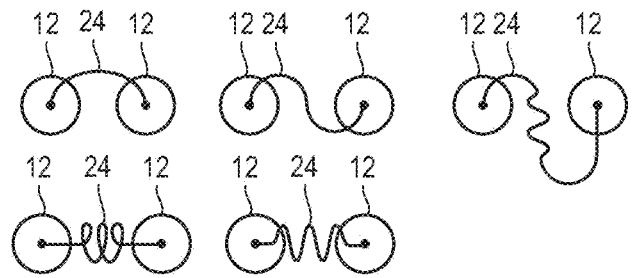
FIG. 6 is a schematic view of various, suitable electrical connections between individual electrochemical cells in the battery assembly, the electrical connections being disposed on and connecting terminals of the individual electrochemical cells.
Figure 7:
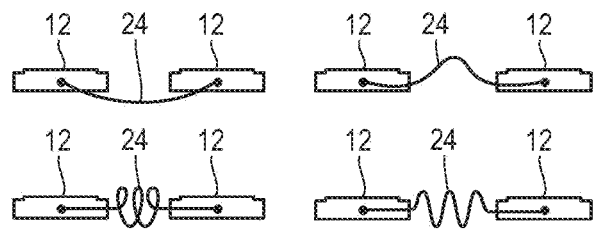
FIG. 7 is a schematic view of various electrical connections between individual electrochemical cells in the battery assembly, the electrical connections being disposed on and connecting cans of the individual electrochemical cells.

Turning now to FIGS. 6 and 7, various types of electrical connections between electrochemical cells 12 are illustrated. In some embodiments, as illustrated in FIG. 6, the flexible conductor 24 may be formed between poles of the individual electrochemical cells 12 on the tops and/or bottoms of the electrochemical cells 12. The flexible conductor 24 may take on various stress relieving shapes, such as loops, offsets, curves, coils, spirals, serpentines, corkscrews, and arcs, which advantageously reduce material stresses when the battery pack assemblies 10 are bent, folded, or stretched. Similarly, as illustrated in FIG. 7, the flexible conductor 24 may be formed between sides of the individual electrochemical cells 12 (for example, because the can of the electrochemical cell is typically electrically connected to a pole) and the flexible conductors 24 may similarly take on stress relieving shapes, such as loops, offsets, curves, coils, spirals, serpentines, corkscrews, and arcs.

The flexible conductors 24 may comprise highly conducting materials that are flexible and resistant to cracking when bent repeatedly. These types of materials, particularly when the materials are formed to provide the conductor 24 with the stress relieving shapes described above, result in the longest usable life of the battery pack assembly 10. In some embodiments, the flexible conductors 24 may comprise copper, nickel, stainless steel, brass, other metals or alloys, carbon fibers, conductive polymers or combinations of these materials. The electrical conductors are relatively thin to allow maximum flexibility without unacceptable Voltage loss during discharge or charge. In some embodiments, the electrical conductors may comprise 36 gage enameled copper magnet wire, which has a diameter of about 0.14 mm. However, diameters of between about 0.05 mm and about 0.5 mm have been found to balance flexibility with failure due to fatigue. Advantageously, flexible conductors with thicknesses in the disclosed ranges generally are more fatigue resistant due to the support given to the flexible conductors by the flexible outer shell. This support, in turn, advantageously allows smaller gage wires to be used than would be possible if the flexible conductors were exposed and not supported by a matrix material, thereby enhancing power characteristics of the battery pack assembly.

The flexible conductors 24 may be attached to the electrochemical cells 12 in various ways; such as resistance welding, ultrasonic welding, laser welding, brazing, soldering or the use of conductive polymers or adhesives.

Figure 8:
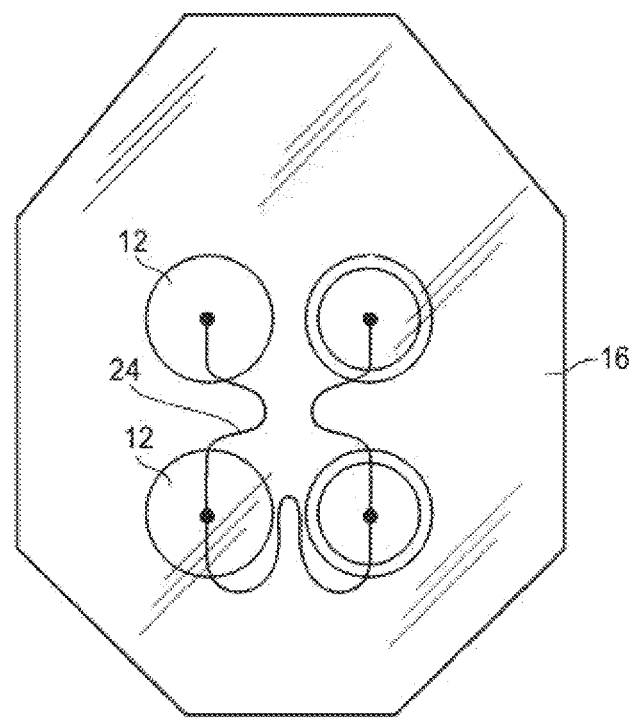
FIG. 8 is a bottom view of one example of a battery pack assembly having electrical connections formed in the top of the electrochemical cells.
Figure 9:
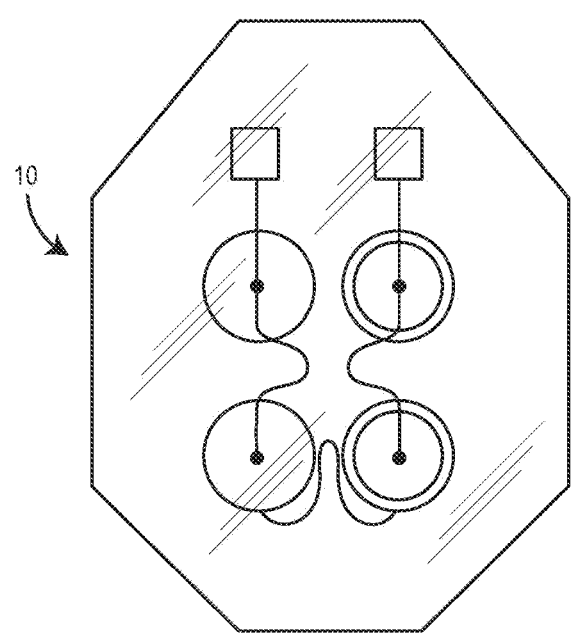
FIG. 9 is a top view of another example of a battery pack assembly having electrical connections formed in the bottom of the electrochemical cells.

FIGS. 8 and 9 illustrate one embodiment of the battery pack assembly 10 comprising an array of electrochemical cells 12 that is embedded in and encapsulated by a matrix of conformable material. In FIG. 8, the flexible conductors 24 on the tops of the electrochemical cells that would otherwise be visible through a clear or translucent conformable material are omitted for clarity. The embodiment of FIGS. 8 and 9 may be formed, for example, by molding the matrix of conformable material around the array of electrochemical cells 12. The electrochemical cells 12 in the array are electrically connected by a flexible conductor 24, as described generally above, and the flexible conductor 24 is further connected to a terminal. The battery pack assembly 10 may advantageously be stretched or twisted without damaging the electrochemical cells 12 or the flexible conductor 24. Furthermore, the stretching and/or twisting advantageously allows the battery pack assembly 10 to conform to another surface, such as a portion of a human body.

FIGS. 10 and 11 illustrate another embodiment of the battery pack assembly 10 comprising an array of electrochemical cells 12 that is surrounded and encapsulated by a matrix of conformable material. The embodiment of FIGS. 10 and 11 may be formed, for example, by laminating the array of electrochemical cells 12 between two sheets of material. The array of electrochemical cells 12 is electrically connected by a flexible conductor 24, as described generally above. The battery pack assembly 10 may advantageously be stretched or twisted without damaging the electrochemical cells 12 or the flexible conductor 24. Furthermore, the stretching and/or twisting advantageously allows the battery pack assembly 10 to conform to another surface, such as a portion of a human body.

Figure 12:
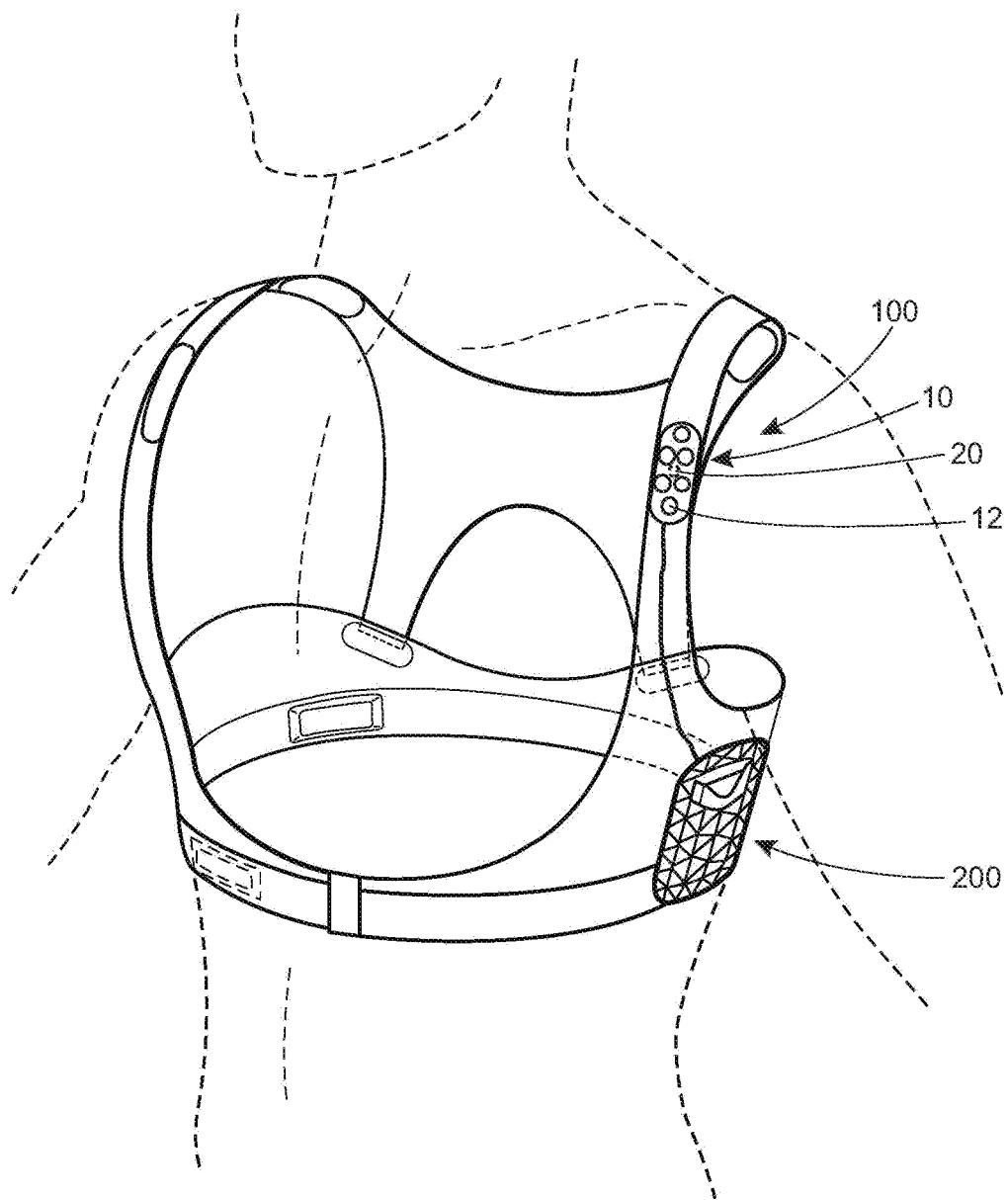
FIG. 12 illustrates a wearable assembly comprising a sensor and a battery pack assembly connected to a medical device.

Turning now to FIG. 12, one example of a wearable garment 100 comprising a battery pack assembly 10 according to the disclosure is illustrated. The battery pack assembly 10 may be located at any point on the wearable garment 100 and the battery pack assembly 10 adjusts its shape to conform to the underlying location on the body. The battery pack assembly 10 comprises the array of individual electrochemical cells 12 and an electronic component 20. The electronic component 20 may comprise a physiological sensor as described above. The electronic component 20 may be communicatively connected to a medical device 200, such as the medical device described above. The medical device 200 monitors a condition and/or administers medical treatment in response to readings from the electronic component 20 when needed.

Example 1

Figure 13:
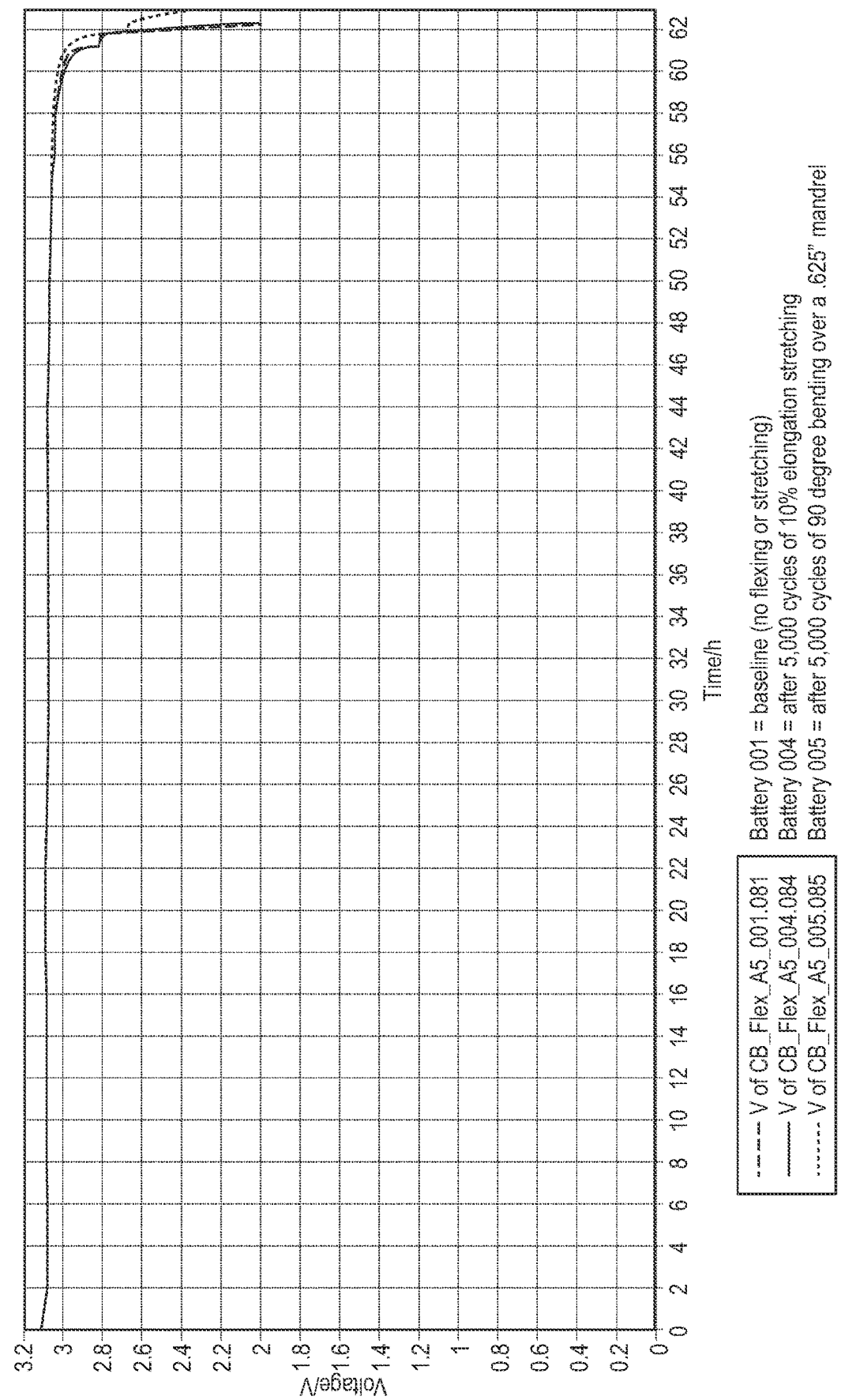
FIG. 13 is a graph of test data collected of one embodiment of a battery pack assembly.

Turning now to FIG. 13, effects on battery performance from stretching and bending, of the outer shell are illustrated. The test configuration included an array of eight SR616 silver oxide button cells in a 2 series by 4 parallel configuration, similar to the arrangement illustrated in FIG. 5C, but with eight total cells instead of the ten illustrated in FIG. 5C. The cells were connected by 36 gage enamel insulated copper wires bent into a serpentine shape and resistance welded to the cell terminals. The assembly was embedded and encapsulated in a silicone rubber, specifically in Smooth-On Dragon Skin™ FX-Pro, which is a silicone rubber having a shore A hardness of 2A, a 100% modulus of 37.8 psi, an elongation break of 763%, and a tensile strength of 288 psi.

The control assembly was discharged at 0.8 mA continuously at room temperature until a voltage of 2.0 V was reached.

Stretching: the assembly was stretched along the long dimension of the outer shell by 10% more than the relaxed dimension continuously for 5,000 cycles. After 5,000 cycles, the assembly was discharged at 0.8 mA continuously at room temperature until a voltage of 2.0 V was reached.

Bending: the assembly was bent over a 0.625" diameter mandrel and then relaxed to its normal shape. Bending cycles were performed at a rate of 22 per minute continuously until 5,000 cycles were achieved. After 5,000 cycles, the battery was discharged at 0.8 mA continuously, at room temperature, until a Voltage of 2.0V was reached.

The results of the tests, as illustrated in FIG. 13, show that the stretching and bending had no significant effect on the electrical performance of the battery assemblies. In fact, electrical performance was nearly indistinguishable between the control assembly and the stretched and bent assemblies. Thus, the individual battery cells were advantageously protected from environmental factors, and surrounded by a material with a skin-like feel without impacting electrical performance.

While certain electrochemical cell 12 array configurations are illustrated herein, electrochemical cells 12 that are spaced apart by substantially regular intervals provide relatively uniform overall mechanical properties and are therefore generally preferred in one embodiment for the user. Specific geometric arrangements of electrochemical cells 12, particularly with three or more axes of bending or axes of symmetry, coupled with the size and geometry of the outer shell material being adapted for the specific use, and with the size and geometry of the electrical interconnections, particularly the stress relieving shapes described above, between cells results in improved flexibility and elasticity of the battery assembly thereby providing greater comfort and enhanced wearability and functionality to the user. Individual electrochemical cells in the array may comprise the same or different sizes and may be circular, oval, rectangular or any other suitable shape. Depending on application requirements, the battery pack assembly 10 may take on virtually any outer shape and may have one or more through holes provided in various locations therein, for example, by omitting an electrochemical cell 12 at the desired location of the hole or by cutting the hole in a desired space between electrochemical cells 12, for example to allow the electronic component 20 to be disposed in the resulting hole such that it can directly contact skin of the user.

The disclosed battery pack assemblies are relatively thin and have mechanical properties similar enough to skin to feel comfortable when attached by a suitable adhesive to a human body. These battery pack assemblies facilitate skin-attached sensors or other devices that can be worn for longer periods of time with less irritation and discomfort to the user. The disclosed battery pack assemblies advantageously provide a continuous, uninterrupted interconnection between the battery contacts and the sensor contacts. While described as facilitating skin contact, it should be understood that the disclosed battery pack assemblies need not be used in this fashion, but instead may be incorporated into an article of clothing such as, for example, and arm band or the article shown in FIG. 12. The skin-like feel allows the disclosed battery assemblies, when worn by a user, to move and thus cause the battery assembly to flex and behave in a manner that enhances user comfort and thus promotes longer term compliance and use. Moreover, the disclosed battery assemblies advantageously protect the cells and electrical connections from environmental factors such as temperature changes, liquids, dirt, dust, etc., while substantially preserving the electrical performance of the battery cells.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A battery pack assembly comprising:
an array of individual electrochemical cells electrically connected to one another, the array of individual electrochemical cells being surrounded and encapsulated by a matrix of conformable material, the matrix of conformable material further providing a protective outer shell, the protective outer shell including a through opening; and
an electronic component disposed in the through opening, wherein the array of individual electrochemical cells is arranged to be electrically connected to the electronic component.

2. The battery pack assembly of claim 1, wherein the electronic component is a physiological sensor.

3. The battery pack assembly of claim 1, wherein the electronic component is a heart rate sensor.

4. The battery pack assembly of claim 1, wherein the electronic component is a temperature sensor.

5. The battery pack assembly of claim 1, further comprising a drug delivery system that is activated by a signal from the electronic component.

6. The battery pack assembly of claim 1, wherein the flexible outer shell comprises an outer shell material including one or more of the following:
a failure stretch ratio of 1.1 to 1.8 and
an ultimate tensile strength between 1 and 50 Mpa.

7. The battery pack assembly of claim 1, wherein the outer shell material comprises an elastomer.

8. The battery pack assembly of claim 1, wherein the outer shell material is laminated around the individual electrochemical cells.

9. The battery pack assembly of claim 1, wherein the outer shell material comprises an adhesive on one side.

10. The battery pack assembly of claim 1, wherein the outer shell material is molded around the electrochemical cells.

11. The battery pack assembly of claim 1, wherein the outer shell material comprises a hardness of between HOOO-S 10 and 90A.

12. The battery pack assembly of claim 1, wherein the outer shell material comprises an elongation break between 10% and 1,000%.

13. A battery pack assembly comprising:
an array of individual electrochemical cells electrically connected with one another, each individual electrochemical cell in the array being surrounded and encapsulated by a matrix of conformable material that forms a flexible outer shell; and
an electronic component operably connected to the array of individual electrochemical cells, the electronic component also being surrounded and encapsulated by the matrix of conformable material,
wherein the matrix of conformable material comprises a material having a hardness between HOO-5 and 30A.

14. The conformable battery pack assembly of claim 13, wherein the electronic component comprises one or more of a processor, a microprocessor, a signal processor, an integrated circuit, a display, a capacitor, a resistor, a transistor, a medical application device such as a glucose delivery device or an automatic defibrillator, a global positioning system (GPS) receiver, a sensor (such as a biometric sensor, a temperature sensor, an accelerometer, a moisture sensor), or an antenna.

15. The conformable battery pack assembly of claim 13, wherein the electronic component is operably connected to a face of one electrochemical cell in the array of individual electrochemical cells.

\* \* \* \* \*